United States Patent [19]

Itoh et al.

[11] 4,432,617

[45] Feb. 21, 1984

[54] EYE REFRACTIVE ERROR MEASURING DEVICE

[75] Inventors: Kiyoshi Itoh, Kamifukuoka; Yukiyasu Nishikawa, Kawagoe; Shuji Hoshika, Fujimi; Ikuzo Okamoto, Tamagawa, all of Japan

[73] Assignee: Asahi Kogaku Kogyo Kabushiki Kaisha, Tokyo, Japan

[21] Appl. No.: 225,221

[22] Filed: Jan. 15, 1981

[30] Foreign Application Priority Data

Jan. 30, 1980 [JP] Japan ................................ 55-9580

[51] Int. Cl.³ .............................................. A61B 3/10
[52] U.S. Cl. .................................................. 351/211
[58] Field of Search ............................... 351/13, 16, 14

[56] References Cited

U.S. PATENT DOCUMENTS 3,880,501  4/1975  Munnerlyn ........................... 351/13
4,266,862  5/1981  Trötscher et al. ................... 351/13
4,272,165  6/1981  Muchel et al. ....................... 351/13
4,306,778  12/1981 Wada et al. .......................... 351/13

Primary Examiner—John K. Corbin
Assistant Examiner—Rodney B. Bovernick
Attorney, Agent, or Firm—Sughrue, Mion, Zinn, Macpeak, and Seas

[57] ABSTRACT

A device for measuring the refractive error of an eye in which refractive powers in a plurality of longitudinal directions are simultaneously measured with a high S-N ratio with a high accuracy. A movable chart is provided in a predetermined direction in a plane perpendicular to an optical axis of an optical system which projects the image of the chart onto the retina of the eye being examined. Measuring means measures the refractive error of the eye in accordance with the state of the optical system at the position thereof at which the image projected onto the retina is in focus. The chart has plural striped patterns which are oriented at different angles from one another.

5 Claims, 7 Drawing Figures

EYE REFRACTIVE ERROR MEASURING DEVICE

BACKGROUND OF THE INVENTION

The present invention relates to a device for measuring the refractive error of the human eye.

The refractive error of the human eye is represented by the refractive power of a spectacle lens used to correct abnormal refraction of the eye, and more specifically by the spherical power, the cylinder power and the cylinder axis errors thereof.

A variety of eye refractive error measuring devices have been proposed in the art. One such device is disclosed in the specification of U.S. Pat. No. 3,888,569 or Japanese Laid-Open Patent Application No. 52893/1979. In a conventional device, the image of a chart is projected onto an eye to be examined by means of an optical system and the state of the optical system at which the image of the chart formed on the retina of the eye becomes most sharp and clear is detected to thereby measure the refractive error of the eye. In the case of an astigmatic eye, the refractive error differs depending on the measuring longitude direction. Therefore, in the conventional device, refractive powers are measured at least in three longitudinal directions and the refractive errors (spherical power, cylinder power and cylinder axis errors) are obtained through calculation from the measured data. In order to carry out the measurement in a plurality of (three or more) longitudinal directions, according to the aforementioned U.S. Pat. No. 3,888,569, a chart is turned to be in various measuring longitudinal directions and the corresponding refractive powers in the various measuring longitudinal directions are measured in a time division manner. Therefore, the device according to U.S. Pat. No. 3,888,569 is disadvantageous in that it takes a relatively long time to achieve all the measurements.

In order to eliminate this difficulty, a technique has been proposed, as discussed in the above-noted Japanese Laid-Open Patent Application No. 52893/1979 whereby various charts are provided for measuring in the different longitudinal directions so that the measurements in all the longitudinal directions are achieved simultaneously. A difficult problem, however, remains to be solved, in that, in the realization of a practical refractive error measuring device, since the intensity of light interfered with by the retina is extremely low and the measurement is interrupted by light reflected by the cornea and the optical system, it is difficult to obtain a sufficiently high S/N ratio (ratio of signal to noise). As described in U.S. Pat. No. 3,888,569, this problem has been solved by scanning the chart itself thereby to separate signal light from noise light according to their frequencies. However, it is difficult to apply the method proposed by the U.S. Patent to the technique of the Japanese Laid-Open Patent Application No. 52893/1979. Thus, the drawback that a sufficiently high S/N ratio cannot be obtained still remains.

Accordingly, an object of the invention is to provide an eye refractive error measuring device in which refractive powers can be simultaneously measured in a plurality of longitudinal directions with a sufficiently high S/N ratio thereby to achieve the desired measurements in a short time and with a high accuracy.

SUMMARY OF THE INVENTION

This, as well as other objects of the invention, are met by an eye refractive error measuring device including a movable chart which is movable in a predetermined direction in a plane perpendicular to an optical axis of the measuring device, an optical system for projecting the image of the movable chart onto the retina of an eye to be examined, and means for measuring the refractive error of the eye from a state of the optical system at a position where the image thus projected appears most sharp, that is, at the position where the image is focused on the retina of the eye. In accordance with the invention, the movable chart is provided with plural striped patterns, each pattern being composed of parallel stripes with the stripes between patterns being oriented at different angles from one another. In one preferred embodiment, the chart has three different patterns, the orientation angles of which relative to one another differ by 60°. In another embodiment, the chart has two different patterns with stripes with the two patterns being orthogonal to one another.

BRIEF DESCRIPTION OF THE DRAWINGS

FIGS. 2A–2C are explanatory diagrams showing a first embodiment of a refractive error measuring device according to the invention of which FIG. 2A is an unfolded diagram showing a part of a scanning chart employed in the device of the invention, FIG. 2B is a plan view of a stationary chart employed in the device of FIG. 2A, and FIG. 2C a sectional view showing the positional relation between the stationary chart and a light receiving member;

FIGS. 3A–3C are explanatory diagrams showing a second embodiment of the device according to the invention of which FIG. 3A is an unfolded diagram showing a part of a scanning chart employed in the second embodiment, FIG. 3B a plan view showing a stationary chart employed in the second embodiment, and FIG. 3C a sectional view showing the positional relation between the stationary chart and a light receiving member.

DESCRIPTION OF THE PREFERRED EMBODIMENTS

The invention will be explained by a detailed description of its preferred embodiments with reference to the accompanying drawings.

Figure 1:
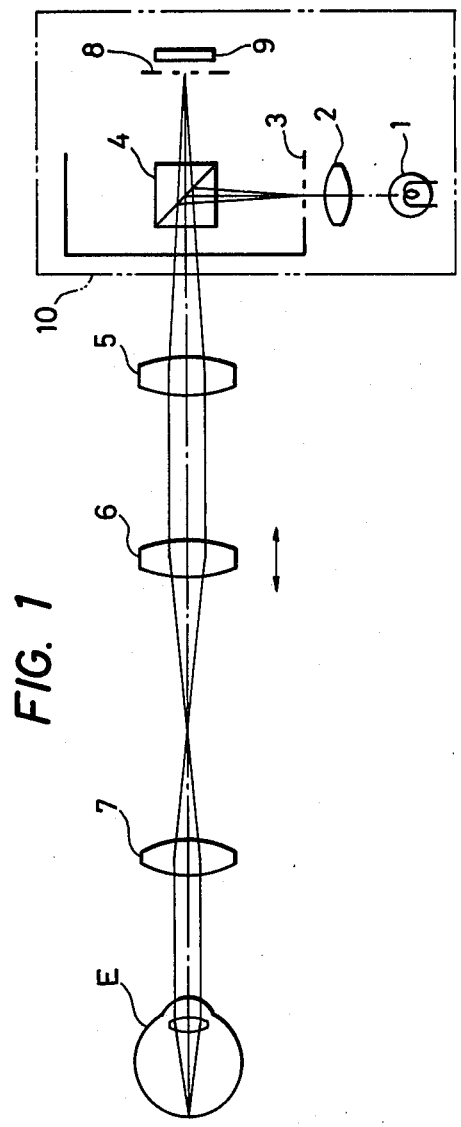
FIG. 1 is an explanatory diagram showing the arrangement of an optical system which is suitable for practicing the invention.

FIG. 1 shows the arrangement of an optical system which is suitable for practicing the invention. Light from a light source 1 is applied through a condenser lens 2 and a scanning chart 3 to a beam splitter 4. A part of the pencil of rays applied to the beam splitter 4 is reflected thereby and then passes through a collimator lens 5, a relay lens 6 and an eyepiece 7 to an eye E to be examined. The pencil of rays applied to the eye E is reflected by the retina of the eye E returning to the beam splitter 4 through the above-described lenses in the opposite direction. A part of the pencil of rays thus returned advances straightly and reaches a light receiving member 9 through a stationary chart 8. The scanning chart 3 and the stationary chart 8 are equally spaced from the beam splitter 4 and are disposed on the rear focus side of the collimator lens 5. (The positional relation "front" and "rear", or "before" and "after", is determined with respect to the eye to be examined as used in the following description.) The relay lens is movable back and forth along the optical axis.

In the optical system thus assembled, the pencil of rays passed through the scanning chart 3 forms an image of the scanning chart 3 at the front focal point of the relay lens and forms it near the retina of the eye E with the aid of the refractive actions of the eyepiece 7 and the eye E. It is assumed that the relay lens 6 is moved from near the eyepiece 7 towards the collimator lens 6. During this movement, the pencil of rays from the eyepiece 7 is changed from a divergent pencil of rays through to a parallel pencil of rays to a convergent pencil of rays. Therefore, initially the position where the image of the scanning chart 3 is formed is behind the retina. However, it approaches the retina gradually and finally it is shifted to a position in front of the retina. During this operation, there is an absolute condition that the image of the scanning chart 3 be formed on the retina (hereinafter referred to as "a focused condition" when applicable). Under this focused condition, the retina and the scanning chart 3, and the retina and the stationary chart 8 are in a conjugate positional relation to one another.

A specific example of an eye refractive error measuring device according to the invention will be described also with reference to the arrangement of the above-described optical system.

Figure 2A:
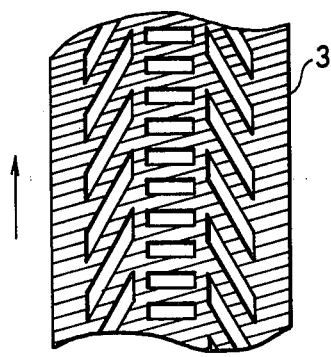
Figure 2B:
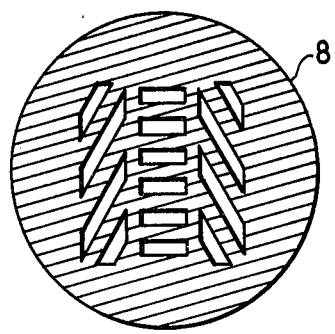
Figure 2C:
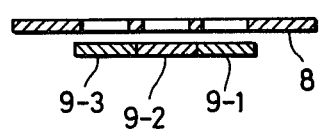

The scanning chart 3 is placed on the side of a rotary cylinder. The pattern, as shown in FIG. 2A, is divided into three regions, namely, a right-hand region, a middle region and a left-hand region, along the axial direction of the rotary cylinder. The slits of the right-hand, middle and left-hand regions are arranged at predetermined intervals at angles of 30°, 90° and 150°, respectively, with respect to the direction of rotation of the rotary cylinder. The pattern of the stationary chart 8 is similar to that of the scanning chart 3, as shown in FIG. 2B. As shown in FIG. 2C, light receiving elements 9-1, 9-2 and 9-3 are disposed behind the stationary chart 8 to detect light passing through the patterns.

The above-described charts are set at the designated positions in the above-described optical system and the cylinder with the scanning chart 3 is rotated at a constant speed in the direction of the arrow. Then, in the focused condition, the stationary chart 8 is scanned with the image of the scanning chart 3 which is a light and dark striped pattern. In this operation, the intensity of light applied to the light receiving elements 9-1, 9-2 and 9-3 through the regions (patterns) of the stationary chart 8 changes at certain frequencies. The amplitudes of the variations of the intensities of light are at a maximum when the focused condition is maintained. Away from the focused condition, the striped pattern projected onto the stationary chart 8 becomes blurry and therefore the amplitude of the intensity variations of the light decreases. The above-described combination of the scanning chart and the stationary chart has a characteristic that the out-of-focus condition in a direction perpendicular to the slits is most sensitively detected. Therefore, in this apparatus, the refractive powers in the longitudinal directions of 30°, 90° and 150° are measured by the patterns in the right-hand, middle and left-hand regions.

With respect to the refractive error, a spherical power S, a cylindrical power C, a cylinder axis angle $\theta$ and a refractive power R at a measuring longitudinal angle $\alpha$ have the following relation:

$$R = S + C \sin^2(\theta + 60).$$

If three sets of measurement data are provided with respect to the measuring longitudinal angle and the refractive power R, then the refractive error can be obtained from the above-formula.

According to this embodiment, the measurement can be achieved by moving the relay lens back and forth only once. Thus, the invention is advantageous in that the measurement can be achieved in a short period of time.

Figure 3A:
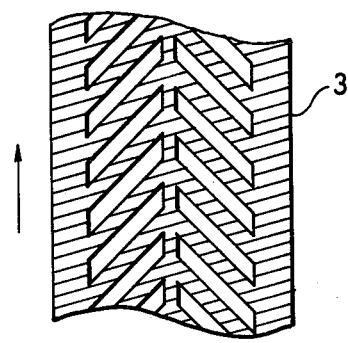
Figure 3B:
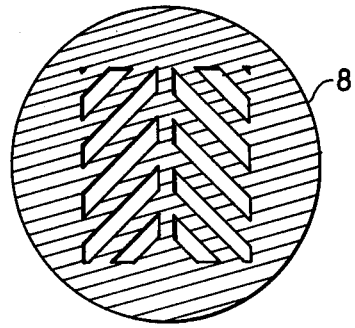
Figure 3C:
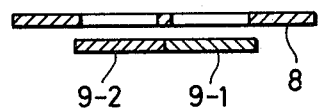

A second embodiment of a device of the invention will be described with reference to FIG. 3 and FIG. 1. In the case of the second embodiment, a part surrounded by the broken line in FIG. 1 (hereinafter referred to as "a light transmitting and receiving section" when applicable) is so designed that it is rotated, as a unit, around the optical axis by an electric motor (not shown). FIG. 3A shows a part of the patterns of a scanning chart 3, FIG. 3B the patterns of a stationary chart 8, and FIG. 3C a sectional view showing the positional relationship between the stationary chart 8 and its light receiving member. As shown in FIG. 3A, the scanning chart 3 is divided into two regions, namely, a right-hand region and a left-hand region. The slits of the right-hand and left-hand regions are arranged at equal intervals at angles of 45° and 135° with respect to the direction of rotation of the cylinder. As in the first example, the pattern of the stationary chart 8 is similar to that of the scanning chart 3. Two light receiving elements 9-1 and 9-2 are provided behind the stationary chart 8, respectively, for the right-hand and left-hand regions of the pattern thereof.

In this arrangement, refractive powers in two orthogonal longitudinal directions can be measured simultaneously. First, the relay lens 6 is moved so that the focused condition is substantially obtained for one of the measuring longitudinal direction. Then, the light transmitting and receiving section is turned around the optical axis until the amplitude of the light incident on the light receiving element becomes a maximum. This is the condition in which the measuring longitudinal angle is coincident with or orthogonal to the cylinder axis angle. Then, the relay lens is moved back and forth again to obtain the refractive powers with respect to the two measuring longitudinal directions. That is, after the cylinder axis angle $\theta$ is set, the refractive powers in the two orthogonal longitudinal directions are obtained. This method is advantageous in that the cylinder power component C of the refractive error can be obtained as the difference between two refractive powers and the spherical power component S can be obtained as one of the refractive powers through a quite simple calculation.

If, in the arrangement of the second embodiment, first the refractive powers in two longitudinal directions are measured at an optical angle, and then the refractive powers in two other longitudinal directions are measured with the light transmitting and receiving section turned, for instance, through 45° so that the refractive power data in four measuring longitudinal directions in total are obtained, then the refractive error can be obtained through the same calculation as that in the first embodiment using three of the four refractive power data points. If, in this case, an average value is obtained from the refractive error thus obtained and a refractive error is obtained from the combination of the other data, the accuracy of measurement will be advantageously improved.

Figure 4:
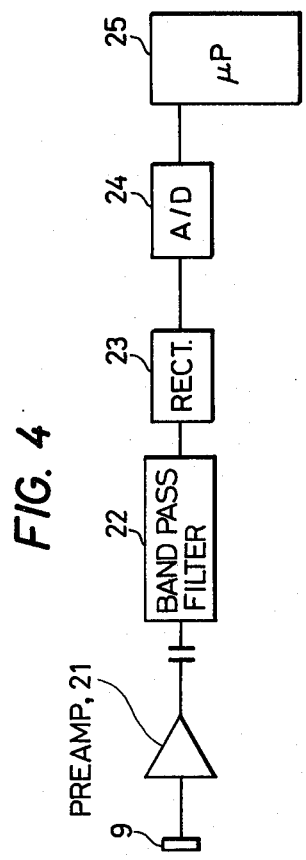
FIG. 4 is a block diagram showing a preferred embodiment of a detection signal processing system of the invention.

Next, a signal processing system will be described with reference to FIG. 4. The system shown in FIG. 4 is shown for only one light receiving element. However, it should be noted that the same system is applicable to the other light receiving elements.

The output detection signal of a light receiving member 9, an optical current, is converted into a voltage signal by a preamplifier 21. The voltage signal is applied to a bandpass filter 22 through which only components in a predetermined frequency range are passed. The signal thus treated is converted into a DC voltage signal proportional to amplitude by a rectifier circuit 23. The DC voltage signal is converted into a digital signal by an analog-to-digital converter 24 which is applied to a microcomputer 25. The central frequency of the bandpass filter 22 is set to the frequency of a received light quantity signal provided when the focusing condition is established in the optical system.

In the combination of the signal processing system thus constructed and the optical system described above, noise components attributed to light reflected by the corneal surface of an examined eye and the surfaces of the optical system components are eliminated by the bandpass filter 22 thus removing any adverse influence from the measurement.

As is clear from the above description, according to the invention, refractive powers in plural longitudinal directions can be measured simultaneously without being affected by light reflected by the corneal surface of the eye to be examined. Accordingly, the refractive error measuring device of the invention achieves measurements in a short time and with high accuracy.

What is claimed is:

1. An eye refractive error measuring device comprising: a chart movable in a predetermined direction in a plane perpendicular to an optical axis of said measuring device, said movable chart having plural striped patterns oriented at different angles from one another; optical system means for projecting the image of said chart onto the retina of an eye to be examined; and means for measuring the refractive error of said eye from a state of said optical system at a position where said image thus projected appears most sharp, said measuring means comprising a stationary chart having patterns similar to said patterns of said movable chart and detecting means, said detecting means receiving light reflected from said retina through said stationary chart.

2. The device as claimed in claim 1 in which said movable and stationary charts each have three different patterns the orientation angles of which are different by 60° from one another.

3. The device as claimed in claim 1 in which said movable and stationary charts each have two different patterns which are orthogonal to one another.

4. The device as claimed in claim 1 wherein said optical system means comprises a light source, a condenser lens, a beam splitter receiving light through said condenser lens from said light source, a collimator lens receiving light from one side of said beam splitter, a relay lens receiving light from said collimator lens, and an eyepiece lens receiving light from said relay lens and directing said light to said eye to be examined.

5. The device as claimed in claim 1 wherein said measuring means further comprises preamplifier means receiving an output signal of said detecting means, bandpass filter means having an input coupled to an output of said preamplifier means, rectifier means having an input coupled to an output of said bandpass filter, analog-to-digital converter means having an input coupled to an output of said rectifier means, and microcomputer means having an input coupled to receive digital outputs of said analog-to-digital converter means.

* * * * *